(12) United States Patent
Muraca

(10) Patent No.: US 9,739,781 B2
(45) Date of Patent: Aug. 22, 2017

(54) ANTI-PHOSPHO-AKT ANTIBODIES

(71) Applicant: Nuclea Biotechnologies, Inc., Pittsfield, MA (US)

(72) Inventor: Patrick J. Muraca, Pittsfield, MA (US)

(73) Assignee: NMDX, LLC, Pittsfield, MA (US)

( * ) Notice: Subject to any disclaimer, the term of this patent is extended or adjusted under 35 U.S.C. 154(b) by 0 days.

(21) Appl. No.: 14/684,945

(22) Filed: Apr. 13, 2015

(65) Prior Publication Data

US 2015/0212085 A1 Jul. 30, 2015

Related U.S. Application Data

(60) Division of application No. 12/618,106, filed on Nov. 13, 2009, now Pat. No. 9,029,512, which is a continuation-in-part of application No. PCT/US2009/045249, filed on May 27, 2009.

(60) Provisional application No. 61/130,198, filed on May 29, 2008.

(51) Int. Cl.

| | |
|---|---|
| *G01N 33/53* | (2006.01) |
| *C12N 5/07* | (2010.01) |
| *C12N 5/16* | (2006.01) |
| *G01N 33/574* | (2006.01) |
| *A61K 31/00* | (2006.01) |
| *A61K 39/395* | (2006.01) |
| *A61K 45/06* | (2006.01) |
| *C07K 16/32* | (2006.01) |
| *G01N 33/68* | (2006.01) |
| *A61K 39/00* | (2006.01) |

(52) U.S. Cl.
CPC ......... *G01N 33/5748* (2013.01); *A61K 31/00* (2013.01); *A61K 39/39558* (2013.01); *A61K 45/06* (2013.01); *C07K 16/32* (2013.01); *G01N 33/68* (2013.01); *A61K 2039/505* (2013.01); *G01N 33/53* (2013.01); *G01N 2333/91205* (2013.01)

(58) Field of Classification Search
None
See application file for complete search history.

(56) References Cited

U.S. PATENT DOCUMENTS

| | | |
|---|---|---|
| 6,670,167 B1 | 12/2003 | Chen et al. |
| 6,723,830 B2 | 4/2004 | Ben-Sasson |
| 6,881,555 B2 | 4/2005 | Guo et al. |
| 2005/0208054 A1 | 9/2005 | Czech et al. |
| 2006/0121496 A1 | 6/2006 | Srivastava et al. |
| 2006/0247188 A1 | 11/2006 | Cheng et al. |

FOREIGN PATENT DOCUMENTS

| | | |
|---|---|---|
| WO | 0037613 | 6/2000 |
| WO | 0056866 | 9/2000 |
| WO | 2006119980 | 11/2006 |

OTHER PUBLICATIONS

Ihle et al., Molecular pharmacology and antitumor activity of PX-866, a novel inhibitor of phosphoinositide-3-kinse signaling. Molecular Cancer Therapeutics, AACR US, Jul. 1, 2004, vol. 3 (7): 763-772.
Barnett et al., Identification and characterization of pleckstrin-homology-domain-dependent isoenzyme-specific Akt inhibitors. Biochem J. Jan. 15, 2005, 385(Pt.2): 399-408.
Arboleda et al., Overexpression of AKT2/protein kinase Beta leads to up-regulation of beta 1 integrins, increased invasion, and metastasis of human breast and ovarian cancer cells. Cancer Res. Jan. 1, 2003, 63(1): 196-206.
Bauer et al., KIT oncogenic signaling mechanisms in imatinib-resistant gastrointestinal stromal tumor: PI3 kinase/AKT is a crucial survival pathway. Oncogene, Nov. 29, 2007; 26(54):7560-7568 Epub Jun. 4.
Tornillo and Terracciano, An update on molecular genetics of gastrointestinal stromal tumors. J. Clin Pathol., Jun. 2006, 59(6): 557-563.
Qian et al., Acyl coenzyme-A binding protein (ACBP) is phosphorylated and secreted by retinal Muller astrocytes following protein kinasr C activation, May 2008, J. Neurochem, 105:1287-1299.

*Primary Examiner* — Hong Sang
(74) *Attorney, Agent, or Firm* — Paula C. Evans

(57) ABSTRACT

The Present invention relates to antibodies that immunospecifically bind to phospho-Akt and certain p-Akt substrates. The invention encompasses human and humanized forms of the antibodies and their use in treating cancers and other proliferative disorders. The invention also relates to p-Akt derived peptides useful for preparing the antibodies. Methods and compositions for detecting, diagnosing, treating or ameliorating a disease or disorder, especially cancer and other proliferative disorders using the present antibodies also are disclosed.

7 Claims, 5 Drawing Sheets

1 2 3

ANTI-PHOSPHO-AKT ANTIBODIES

RELATED APPLICATIONS

This application is a Divisional application of U.S. patent application Ser. No. 12/618,106, filed Nov. 13, 2009, which is a Continuation-in-Part and claims the benefit under 35 U.S.C. 365(c) of PCT Application No. PCT/US09/45249, filed 27 May 2009, which in turn claims the benefit under 35 U.S.C. 119(e) of U.S. Provisional Application Ser. No. 61/130,198, filed 29 May 2008, the content of each of which is incorporated herein by reference in their entirety.

REFERENCE TO THE SEQUENCING LISTING

The present application is being filed along with a Sequence Listing in electronic format. The Sequence Listing is provided as a file entitled 20151013USDIVSEQLST.txt, created on Apr. 13, 2015 which is 2,219 bytes in size. The information in the electronic format of the sequence listing is incorporated herein by reference in its entirety.

FIELD OF THE INVENTION

The present invention relates to antibodies and related molecules that immunospecifically bind to and inhibit the activity of phosphor-Akt and certain Akt substrates. The invention relates to methods and compositions for preventing, detecting, diagnosing, treating or ameliorating a proliferative disease using the present antibodies.

BACKGROUND OF THE INVENTION

Akt (v-akt murine thyoma viral oncogene), also referred to as PKB or Rae, plays a critical role in controlling survival and apoptosis. Franke, T. F. (1997) *Cell*, 88: 435-437. This serine-threonine protein kinase is activated by insulin and various growth and survival factors, and functions in a wortmannin-sensitive pathway involving PI3 kinase (Burgering, B. T. and Coffer, P. J. (1995) *Nature*, 376, 599-602; Franke, T. F. et al. (1995) *Cell*, 81: 727-736). Akt is activated by phospholipid binding and activation loop phosphorylation at Thr308 by PDK1 and by phosphorylation within the carboxy terminus at Ser473 (Alessi, D. R. et al. (1996) *EMBO J.*, 15, 6541-6551). The previously elusive PDK2 responsible for phosphorylation of Akt at Ser473 has been identified as mammalian target of rapamycin (mTOR) in a rapamycin-insensitive complex with rictor and Sinl (Sarbassov, D. D. et al., (2005), *Science*, 307: 1098-1101; Jacinto, E. et al., (2006), *Cell*, 127: 125-137).

Akt promotes cell survival by inhibiting apoptosis through its ability to phosphorylate and inactivate several targets, including Bad, forkhead transcription factors, c-Raf and caspase-9. Cardone, M. H. et al., (1998), *Science*, 282: 1318-1321; Brunet, A. et al., (1999), *Cell*, 96: 857-868; Zimmerman, S. et al., (1999), *Science*, 286: 1741-1744. PTEN phosphatase is a major negative regulator of the PI3 kinase/Akt signaling pathway. Cantley, L. C. et al., (1999), *Proc. Natl. Acad. Sci., USA*, 96: 4240-4245. LY294002 is a specific PI3 kinase inhibitor. Vlahos, C. et al., (1994), *J. Biol. Chem.*, 269: 5241-5248. One of the essential functions of Akt is the regulation of glycogen synthesis through phosphorylation and inactivation of GSK-3a and •Akt may also play a role in insulin stimulation of glucose transport (Hajduck, E. et al., (2000), *FEES Lett.*, 492: 199-203; Cross, D. A. et al., (1995), *Nature*, 373: 785-789).

In addition to its role in survival and glycogen synthesis, Akt is involved in cell cycle regulation by preventing GSK-3 mediated phosphorylation and degradation of cyclin Dl, and by negatively regulating the cyclin dependent kinase inhibitors p27 Kip and p21 Wafl. Diehl, J. A. et al., (1998), *Genes Dev.*, 12: 3499-3511; Gesbert, F. et al., (2000), *J. Biol. Chem.*, 275: 39223-39230; Zhou, B. P. et al., (2001), *Nat. Cell Biol*; 3: 245-252. Akt also plays a critical role in cell growth by directly phosphorylating mTOR in a rapamycin-sensitive complex containing raptor. Nave, B. T. et al., (1999), *Biochem. J.*, 344: 427-431. More importantly, Akt phosphorylates and inactivates tuberin (TSC2), an inhibitor of mTOR within the mTOR-raptor complex. Manning, B. D. et al., (2003), *Biochem. Soc. Trans.*, 31(3): 573-8 Inhibition of mTOR stops the protein synthesis machinery due to inactivation of its effector p70 S6 kinase and activation of the eukaryotic initiation factor, 4E binding protein 1 (4EEP1), an inhibitor of translation. Manning, B. D. et al., (2002), *Mol. Cell*, 10: 151-162; Inoki, K. et al., (2002), *Nat. Cell Biol.*, 4: 648-657.

The SH3 domain of the tyrosine kinase Src interacts with a PXXP motif of Akt, and Src activates Akt by phosphorylating Tyr315 and Tyr326. These phosphorylation events are thought to occur prior to the phosphorylation of Thr308 and Ser473. In addition, Src inhibits PTEN, which results in a decrease of dephosphorylation of Ptdlns and increased phosphorylation of Akt. Lu, Y. et al., (2003), *J Biol Chem.*, 278(41): 40057-40066; Signoretti et al., *J. Nat. Cancer Inst.*, (2000), Vol. 92(23): 1918.

SUMMARY OF THE INVENTION

The invention comprises antibodies that specifically target total Akt, including phospho-Akt, and total ERK, including phospho-ERK, peptides useful for generating the antibodies, and diagnostic, prognostic and therapeutic methods of using the antibodies. The antibodies of the present invention are specific for a peptide sequence conserved among Akt and some substrates of Akt, including ERK. The antibodies of the present invention preferentially recognize peptides and proteins containing at least a portion of the peptide sequence in a manner substantially independent of the surrounding amino acid sequence. In a preferred aspect, the invention comprises monoclonal antibodies that specifically inhibit overproduction, but not normal production, of phospho-Akt (p-Akt), and/or inhibit binding of Akt and/or phospho-Akt to their receptors.

The present monoclonal antibodies may be raised in a mammalian species or may be produced in vitro. In one embodiment, the monoclonal antibodies of the present invention are raised by immunizing the mammal with a peptide or mixture of peptides derived from an Akt protein in which a serine and/or threonine residue within the peptide is phosphorylated. In another embodiment, the monoclonal antibodies are prepared by an in vitro process using cells. In a preferred embodiment, the present monoclonal antibodies are humanized or human. The immunogenic peptides used to raise the antibodies also form a part of this invention.

Monoclonal anti-pAkt antibodies of the present invention include monoclonal antibodies or antibody fragments, half-antibodies, hybrid derivatives, probes, and other molecular constructs. These antibodies binding portions thereof, probes, or ligands, are highly specific for p-Akt or p-Akt pathway proteins, including ERK and phospho-ERK. Humanized or human monoclonal antibodies of the present invention are useful as therapeutic agents for treating neoplastic or proliferative diseases in which aberrant expression, particularly overexpression of p-Akt is implicated.

The invention further comprises polyclonal antibodies raised using the immunogenic peptides of the invention. The monoclonal and polyclonal antibodies of the present invention may be used as diagnostic or prognostic reagents. In this embodiment, the antibodies may be included in a kit for use in an immunohistochemistry procedure.

Another aspect of the present invention relates to methods of detecting cancerous tissue in a biological sample. This method involves contacting a biological sample of a person suspected of having cancer with an anti-p-Akt antibody of the present invention labeled with a detectable label. The biological sample is contacted with the antibody having a label under conditions effective to permit binding of the antibody to the cancerous tissue in the biological sample. The presence of cancerous tissue in the biological sample is detected by detection of the label. For this purpose, the antibody may be monoclonal or polyclonal.

BRIEF DESCRIPTION OF THE FIGURES

FIG. 3B shows little or no staining in tissue 24 hours after treatment with the NU-1001-41 antibody.

FIGS. 4A and 4B show the staining patterns in glioblastoma cell line SF-295 using a commercial p-Akt antibody; FIG. 3A shows intense staining in untreated SF-295 cells, and FIG. 3B shows little or no staining in SF-295 cells 24 hours after treatment with the NU-1001-41 antibody.

DETAILED DESCRIPTION OF THE INVENTION

Figure 1:
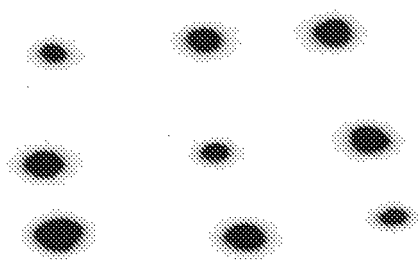
FIG. 1 is a Western dot blot showing the reactivity of three monoclonal antibodies of the invention with p-Akt protein.

The present invention encompasses antibodies, including antibody fragments, that immunospecifically bind to a p-Akt protein, fragment or a variant of p-Akt, as well as certain p-Akt substrates, including ERK and p-ERK. In particular, the invention encompasses antibodies or fragments thereof that immunospecifically bind to a p-Akt protein comprising at least about six consecutive amino acids up to the full length of any of the polypeptides of SEQ ID NOs. 1-6. The monoclonal antibodies of the present invention inhibit the signaling pathway of phospho-Akt thereby promoting apoptosis in proliferating cells. It is believed that binding of the present antibodies in vivo leads to inhibition of the signaling emanating from Akt and directed to intracellular factors involved in the regulation of cell proliferation and cellular death, and/or inhibit binding of Akt and/or phospho-Akt to their receptors.

In one aspect, the present invention relates to methods and compositions for preventing, treating or ameliorating a disease or disorder characterized by abnormal proliferation of cells comprising administering to an animal, preferably a human, a therapeutically effective amount of one or more monoclonal antibodies or fragments thereof that immunospecifically bind to and inhibit a p-Akt protein or polypeptide sequence, or variant thereof. In a preferred embodiment, the present invention relates to methods and compositions for preventing, treating or ameliorating a disease or disorder associated with p-Akt function, p-Akt substrate function or aberrant p-Akt expression, comprising administering to an animal, preferably a human, a therapeutically effective amount of one or more monoclonal antibodies or fragments thereof that immunospecifically bind to p-Akt, or a variant thereof. In highly preferred embodiments, the present invention relates to antibody-based methods and compositions for preventing, treating or ameliorating cancers and other proliferative disorders characterized by aberrant expression of p-Akt. The preferred p-Akt antibodies are specific for all or a portion of the peptide sequence of SEQ ID NOs. 1-6.

In a preferred embodiment, human or humanized monoclonal antibodies of the present invention are used in methods and compositions for preventing, treating or ameliorating cancer, including but not limited to, the following types of cancer: breast cancer, lung cancer, colon cancer, cancer of the urinary tract, bladder cancer, kidney cancer, pancreatic cancer, liver cancer, stomach cancer, prostate cancer, leukemia, Non-Hodgkin's lymphoma, esophageal cancer, brain cancer, leukemia, ovarian cancer, testicular cancer, melanoma, uterine cancer, cervical cancer, cancer of the larynx, rectal cancer, and cancers of the oral cavity. In a preferred embodiment, the cancer is characterized by aberrant expression of p-Akt; preferably, the patient is tested for p-Akt expression prior to treatment. Testing may be carried out on a sample of the patient's tumor using standard immunohistochemistry techniques with the antibodies of the present invention, or a commercial antibody that detects p-Akt expression. The antibodies of the present invention may be administered alone, or in combination with chemotherapeutic agents such as paclitaxel (Taxol®), irinotecan (Camptosar®, CPT-11), 5-fluroruracil (5-FU, Adrucil®), cyclophosphamide (Cytoxan®), imatinib mesylate (Gleevec®) or methotrexate, or other therapeutic agents useful in the treatment of cancers.

The present invention also encompasses methods and compositions for detecting, diagnosing, or prognosing diseases or disorders comprising administering to an animal, preferably a human, an effective amount of an antibody or fragment thereof that immunospecifically binds to p-Akt or variant thereof, or to certain p-Akt substrates, comprising at least a portion of the sequence of a peptide of SEQ ID NO. 1-6. The present invention also encompasses methods and compositions for detecting, diagnosing, or prognosing diseases or disorders associated with p-Akt function or aberrant p-Akt expression, comprising administering to an animal, preferably a human, an effective amount of an antibody or fragment thereof that immunospecifically binds to p-Akt or a variant thereof comprising at least a portion of the sequence of a peptide of SEQ ID NO. 1-6. In a preferred embodiment, the disease is cancer or other proliferative disorder characterized by aberrant expression of p-Akt.

In preferred aspect, the antibodies are human or humanized monoclonal antibodies that are suitable for human therapeutic use. The present monoclonal antibodies are highly specific for p-Akt, which is implicated in many cancers. The monoclonal antibodies of the present invention further encompass fragments or variants of these antibodies (e.g., VH domains, VH CDRs, VL domains, or VL CDRs), that immunospecifically bind to, and inhibit, p-Akt or variants thereof comprising at least a portion of the sequence of a peptide of SEQ ID NO. 1-6. The present monoclonal antibodies or fragments thereof also may bind to and inhibit the activity of certain substrates of p-Akt that contain at least a portion of the sequence of a peptide of SEQ ID NO. 1-6.

The present invention also comprises non-human monoclonal antibodies and polyclonal antisera that bind p-Akt which can be used as diagnostic or prognostic reagents. The non-human antibodies of the present invention may be linked to a detectable label, such as an enzyme, a fluorescent label, a luminescent label, or a bioluminescent label. The present invention also provides antibodies that bind p-Akt polypeptides which are coupled to a therapeutic or cytotoxic agent. The present invention also provides antibodies that bind p-Akt polypeptides which are coupled to a radioactive material.

Another aspect of the present invention comprises methods of using of the antibodies of the present invention as a diagnostic tool to monitor the expression of p-Akt in vitro, e.g., in a tumor biopsy specimen, using immunohistochemistry techniques.

The antibodies of the present invention can be produced by using well-established techniques for producing monoclonal and polyclonal antibodies, using the p-Akt peptides of SEQ ID NO. 1-6 as immunogens.

Phospho-Akt Peptides

The present invention provides novel isolated p-Akt peptides, as well as mixtures containing two or more p-Akt peptides.

As used herein, the term "peptide" refers to a natural or synthetic molecule comprising two or more amino acids linked by the carboxyl group of one amino acid and the amino group of another. A peptide of the present invention is not limited by length, thus the term encompasses "polypeptide" and "protein". A "p-Akt peptide" of the present invention is a peptide fragment derived from a kinase protein and is preferably between about 6 to about 100 amino acids in length, more preferably between about 8 to about 50 amino acids in length, more preferably between about 10 to about 35 amino acids in length. The terms "polypeptide" and "protein" sometimes are used interchangeably. A "p-Akt polypeptide" may refer to an entire p-Akt protein, or to a fragment or variant thereof. Preferably, the p-Akt peptides of the present invention contain an epitope for the production of an antibody specifically immunoreactive to the p-Akt peptide.

In a preferred embodiment, the peptides of the present invention comprise a peptide containing an epitope, either an immunogenic epitope or an antigenic epitope. An "immunogenic epitope" as used herein, refers to a portion of a peptide that elicits an antibody response in an animal, as determined by any method known in the art, for example, by the methods for generating antibodies described herein. See, for example, Geysen et al., 1983, *Proc. Natl. Acad. Sci. USA*, 81:3998-4002. The term "antigenic epitope" as used herein refers to a portion of a protein to which an antibody can immunospecifically bind to its antigen as determined by any method well known in the art, for example, by the immunoassays described herein. Antigenic epitopes need not necessarily be immunogenic. Peptides that function as epitopes may be produced by any conventional means. See, e.g., Houghten, 1985, *Proc. Natl. Acad. Sci. USA*, 82:5131-5135; and as described in U.S. Pat. No. 4,631,211.

As used herein, the term "isolated," with respect to peptides, nucleic acids, or antibodies, refers to that the material is removed from its original environment (e.g., the natural environment if it is naturally occurring). For example, a naturally-occurring nucleic acid or peptide or antibody present in a living animal is not isolated, but the same nucleic acid or peptide or antibody, which is separated from some or all of the coexisting materials in the natural system, is isolated. Such isolated nucleic acid could be part of a vector and such isolated nucleic acid or peptide or antibody could be part of a composition, and still be isolated in that the vector or composition is not part of its natural environment. An "isolated" peptide, nucleic acid or antibody, also includes material synthesized, or produced by recombinant DNA technology, as well as preparations such as serum containing an antibody of the invention.

In one embodiment, the p-Akt peptide of the invention is synthesized by methods known in the art and as described below. In another preferred embodiment, the p-Akt peptide is produced by expressing a nucleic acid encoding the peptide in a cell.

P-Akt peptides can be synthesized by methods well known in the art. Synthetic methods that can be used include, for example, ribosomally-directed fermentation methods, as well as non-ribosomal strategies and chemical synthesis methods. P-Akt peptides containing the 20 natural amino acids can be prepared via recombinant expression systems that utilize the ribosomally directed peptide synthesis machinery of a host organism, e.g., *E. coli*. Alternatively, p-Akt peptides, including those containing unnatural or non-proteinogenic amino acids or modified amino acid side chains can be prepared through a solution-phase chemical synthesis of peptides (e.g., using N-Boc protection and the activated ester route). Protocols for sequence solution-phase chemical synthesis of peptides have been described in Andersson et al., *Biopolymers*, 55:227-250 (2000). One method used for generating peptides is solution-phase chemical synthesis, which employs a N-tert-butoxy (N-Boc) protected amino acid and a C-protected amino acid. Andersson et al., supra. An alternative solution-phase method for chemically-catalyzed peptide synthesis employs pre-activated esters as the carboxyl component for coupling Andersson et al., supra. In addition, enzyme-mediated solid-phase peptide synthesis has also been employed. Solid-phase peptide synthesis (SPPS) uses insoluble resin supports, and has simplified and accelerated peptide synthesis and facilitated purification. Merrifield, R. B., *J. Am. Chem. Soc.*, 85:2149-2154 (1963). Since the growing peptide is anchored on an insoluble resin, unreacted soluble reagents can be removed by simple filtration or washing without manipulative losses. Solid phase peptide synthesis can be performed using automation. Those skilled in the art will recognize that various peptides are within the spirit and scope of the present invention.

The p-Akt peptides according to the present invention can be modified, for example, by the addition of an acetyl or amine group or amino acids at the amino- and/or carboxy-terminus of the peptide. Amino acid addition modifications may also be performed, for example, to alter the conformation of the epitope bearing peptide such that the epitope will have a conformation more closely related to the structure of the epitope in the native protein. An example of a modified epitope-bearing peptide of the invention is a peptide in which one or more cysteine residues have been added to the peptide to allow for the formation of a disulfide bond between two cysteines, thus resulting in a stable loop structure of the epitope-bearing peptide under non-reducing conditions. Disulfide bonds can form between a cysteine residue added to the peptide and a cysteine residue of the naturally-occurring epitope, or between two cysteines which have both been added to the naturally-occurring epitope-bearing peptide.

In addition, it is possible to modify one or more amino acid residues of the peptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing peptides contemplated by this invention include biotinylation.

In one embodiment, the p-Akt peptides of the invention is modified by adding an acetyl group at the amino terminus and/or an amide group at the carboxyl terminus.

The p-Akt peptides of the invention may be provided as a chimeric peptide, such as in the form of a fusion peptide. For instance, the p-Akt peptide can be provided as a recombinant fusion peptide which includes a second peptide portion having an amino acid sequence unrelated (heterologous) to the p-Akt peptide. For example, the second peptide portion may be glutathione-S-transferase, or a peptide with an enzymatic activity such as alkaline phosphatase, or an epitope tag.

In a preferred embodiment, the p-Akt peptide contains an amino acid sequence that is identical with or homologous to all or a portion containing at least six consecutive amino acids of a sequence represented by any one of SEQ ID NOs. 1-6. A homologous sequence is at least about 70%, 75%, 80%, 85%, 90% or 95% identical to the peptide represented by any one of SEQ ID NOs. 1-6.

P-Akt Peptides:

| | |
|---|---|
| SEQ ID NO. 1 | FYGAEIVSAL DYLHSGKIVY R |
| SEQ ID NO. 2 | DKKLVPPFKP QVTSETDTRY FDEEFTAQTI T |
| SEQ ID NO. 3 | QWTTVIERTF HVETPEEREE WTTAIQTVAD |
| SEQ ID NO. 4 | FSEDRARFYG AEIVSALDYL HSEKNVVYRD LKL |
| SEQ ID NO. 5 | FVMEYVNGGE LFFHLSRE |
| SEQ ID NO. 6 | EDIKFPRTLS SDAKSLLSGL LIKDPNKRLG GGP |

In a preferred embodiment, the p-Akt peptide is encoded by a nucleic acid containing any combination of nucleotide degeneracy.

The invention also provides a mixture of two or more p-Akt peptides, each containing an amino acid sequence that is identical with or homologous to a sequence represented in SEQ ID NOs. 1-6. In a preferred embodiment, the mixture contains two peptides, each containing an amino acid sequence that is identical with or homologous to a sequence represented in SEQ ID NOs. 1 and 2; SEQ ID NOs. 3 and 4; or SEQ ID Nos. 5 and 6.

The peptides may be derivatized e.g., by conjugation with bovine serum albumin (BSA), or keyhole limpet hemocyanin (KLH), and/or with a functional group such as hydroxy (—OH), acetyl (—CH$_2$COOH) or amide (—NH$_2$).

Antibodies Against p-Akt

The present invention also provides antibodies that are specifically immunoreactive with the p-Akt peptides and p-Akt proteins containing at the p-Akt peptide sequences as described above. The antibodies may be polyclonal or monoclonal or recombinant, produced by methods known in the art or as described below.

As use herein, the term "specifically immunoreactive" refers to a measurable and reproducible specific immunoreaction such as binding between a peptide and an antibody that is determinative of the presence of the peptide in the presence of a heterogeneous population of peptides and other biologics. The term "specifically immunoreactive" may include specific recognition of structural shapes and surface features. Thus, under designated conditions, an antibody specifically immunoreactive to a particular peptide does not bind in a significant amount to other peptides present in the sample. An antibody specifically immunoreactive to a peptide has an association constant of at least about $10^3 M^{-1}$ or $10^4 M^{-1}$ sometimes about $10^5 M^{-1}$ or $10^6 M^{-1}$, in other instances $10^6 M^{-1}$ or $10^7 M^{-1}$, preferably about $10^8 M^{-1}$ to $10^9 M^{-1}$ and more preferably, about $10^{10} M^{-1}$ to $10^{11} M^{-1}$ or higher. A variety of immunoassay formats can be used to determine antibodies specifically immunoreactive to a particular peptide. For example, solid-phase ELISA immunoassays are routinely used to select monoclonal antibodies specifically immunoreactive with a peptide. See, e.g., Harlow and Lane (1988), Antibodies, A Laboratory Manual, Cold Spring Harbor Publications, New York, for a description of immunoassay formats and conditions that can be used to determine specific immunoreactivity.

As used herein, the term "antibody" refers to an immunoglobulin specifically immunoreactive to a given antigen (e.g., a p-Akt peptide of the invention). The term "antibody" as used herein is intended to include whole antibodies of any isotype (IgG, IgA, IgM, IgE, etc.), and fragments thereof. An "antibody" of the invention also includes an antibody preparation, e.g., a serum (antiserum). Antibodies can be fragmented using conventional techniques and the fragments screened for utility in the same manner as whole antibodies. Thus, the term includes segments of proteolytically-cleaved or recombinantly-prepared portions of an antibody molecule that selectively reacts with a certain protein or peptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFvs may be covalently or non-covalently linked to form antibodies having two or more binding sites. Antibodies may be labeled with detectable labels by one of skill in the art. The label can be a radioisotope, fluorescent compound, chemiluminescent compound, enzyme, or enzyme co-factor, or any other labels known in the art. In some aspects, the antibody that binds to an entity one wishes to measure (the primary antibody) is not labeled, but is instead detected by binding of a labeled secondary antibody that specifically binds to the primary antibody.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the invention can be from any animal origin including birds and mammals. Preferably, the antibodies are of human, murine (e.g., mouse and rat), donkey, sheep, rabbit, goat, guinea pig, camel, horse, or chicken origin.

As used herein, a "monoclonal antibody" refers to an antibody that recognizes only one type of antigen. This type of antibodies is produced by the daughter cells of a single antibody-producing hybridoma. A monoclonal antibody typically displays a single binding affinity for any epitope with which it immunoreacts. A monoclonal antibody may contain an antibody molecule having a plurality of antibody combining sites, each immunospecific for a different epitope, e.g., a bispecific monoclonal antibody. Monoclonal antibodies may be obtained by methods known to those skilled in the art. Kohler and Milstein (1975), *Nature*, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), Antibodies: A Laboratory Manual, Cold Spring Harbor Laboratory; Colligan et al. (1992, 1993), eds., CmTent Protocols in Immunology, Greene Publishing Assoc. and Wiley Interscience, N.Y.; Iyer et al., *Ind. J Med. Res.*, (2000), 123:561-564.

The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. See, e.g., WO 93/17715; WO92/08802; WO 91/00360; WO 92/05793; Tutt et al., 1991, *J Immunol.*, 147:60-69; U.S. Pat. Nos. 4,474,893; 4,714,681; 4,925,648; 5,573,920; 5,601,819; and Kostelny et al., 1992, *J. Immunol.*, 148:1547-1553. For example, the antibodies may be produced against a peptide containing repeated units of a p-Akt peptide sequence of the invention, or they may be produced against a peptide containing two or more p-Akt peptide sequences of the invention, or the combination thereof.

Moreover, antibodies can also be prepared from any region of the p-Akt peptides of the invention. In addition, if a polypeptide is a receptor protein, e.g., a receptor p-Akt, antibodies can be developed against an entire receptor or portions of the receptor, for example, an intracellular domain, an extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example.

In the present invention, the p-Akt peptides for generating antibodies preferably contain a sequence of at least about 6, at least about 7, more preferably at least about 8, at least about 9, at least about 10, at least about 11, at least about 12, at least about 13, at least about 14, at least about 15, and, preferably, between about 5 to about 50 amino acids in length, more preferably between about 10 to about 35 amino acids in length. The preferred p-Akt peptides are those having an amino acid sequence the same as or homologous to all or a portion of the sequence of the peptides of SEQ ID NOs. 1-6.

The human, humanized or non-human monoclonal antibodies of the present invention can be prepared using well-established methods. In one embodiment, the monoclonal antibodies are prepared using hybridoma technology, such as those described by Kohler and Milstein (1975), *Nature*, 256:495. In a hybridoma method, a mouse, hamster, or other appropriate host animal, is typically immunized with an immunizing agent (e.g., a p-Akt peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell. Goding, Monoclonal Antibodies: Principles and Practice, Academic Press, (1986) pp. 59-1031. Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J Immunol.* (1984), 133:3001; Brodeur et al., Monoclonal Antibody Production Techniques and Applications, Marcel Dekker, Inc., New York, (1987) pp. 51-63; Fukuma et al., *Autoimmunity*, 10(4):291-195 (1991).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding specificity of the monoclonal antibody can, for example, be determined by the Scatchard analysis of Munson and Pollard (1980), *Anal. Biochem.*, 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Polyclonal antibodies of the invention can also be produced by various procedures well known in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100-tg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Antibodies encompassed by the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv, or disulfide stabilized antibody domains recombinantly fused to either the phage polynucleotide III or polynucleotide VIII protein. Examples of phage display methods that can be used to make the antibodies of the present invention include those disclosed in Brinkman et al. (1995) *J Immunol. Methods,* 182:41-50; Ames et al. (1995) *J Immunol. Methods,* 184:177-186; Kettleborough et al. (1994) Eur. J. Immunol., 24:952-958; Persic et al. (1997) *Gene,* 187:9-18; Burton et al. (1994) *Advances in Immunology,* 57:191-280; PCT application No. PCT/GB91/01134; PCT publications WO 90/02809; WO 91110737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce antibody fragments such as single-chain Fvs and antibodies include those described in U.S. Pat. Nos. 4,946,778 and 5,258, 498; Huston et al. (1991) *Methods in Enzymology,* 203:46-88; Shu et al. (1993) *Proc. Natl. Acad. Sci. USA,* 90:7995-7999; and Skerra et al. (1988) *Science,* 240:1038-1040, each of which is incorporated herein by reference in its entirety.

For some uses, including the in vivo use of antibodies in humans and in vitro detection assays, it is preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. See, e.g., Morrison (1985), *Science,* 229:1202; Oi et al. (1986), *BioTechniques,* 4:214; Gillies et al. (1989), *J Immunol. Methods,* 125:191-202; and U.S. Pat. Nos. 5,807,715; 4,816,567; and 4,816,397, which are incorporated herein by reference in their entirety.

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. See, e.g., Queen et al., U.S. Pat. Nos. 5,693,762 and 5,585,089; and Riechmann et al. (1988) *Nature,* 332:323, which are incorporated herein by reference in their entireties. Antibodies can be humanized using a variety of techniques known in the art, including, for example, CDR-grafting (EP 239, 400; PCT publication WO 91/09967; U.S. Pat. Nos. 5,225,539; 5,530,101; and 5,585, 089); veneering or resurfacing (EP 592,106; EP 519,596; Padlan (1991), *Molecular Immunology,* 28(4/5):489-498; Studnicka et al. (1994) *Protein Engineering,* 7(6):805-814; Roguska et al. (1994) *Proc. Natl. Acad. Sci. USA,* 91:969-973; and chain shuffling (U.S. Pat. No. 5,565,332).

Completely human antibodies are particularly desirable for therapeutic treatment of human patients, so as to avoid or alleviate immune reaction to foreign protein. Human antibodies can be made by a variety of methods known in the art, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (1995) Inti. Rev. Immunol., 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies. Preferred methods for producing human monoclonal antibodies of the present invention are those described in Nash et al., Immunology, 68:332-340 (1989) and Fukuma et al., Autoimmunity, 10(4):291-195 (1991).

Once an antibody molecule of the invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In one embodiment, the present invention provides human or humanized monoclonal antibodies that specifically immuoreact to a p-Akt protein, or fragment or variant thereof. In a preferred embodiment, the invention provides a novel monoclonal antibody that specifically recognizes a sequence comprising at least about 6 up to the entire sequence of a peptide selected from the group consisting of SEQ ID NOs. 1-6.

The invention further provides a mixture containing two or more monoclonal antibodies produced as described above. In a preferred embodiment, the mixture contains two or more monoclonal antibodies raised against different p-Akt peptides derived from the same p-Akt protein. In another preferred embodiment, the mixture contains two or more monoclonal antibodies raised against different p-Akt peptides, at least two of which are derived from different p-Akt proteins.

In a currently preferred embodiment, the antibody mixture contains two or more antibodies raised against peptides comprising an amino acid sequence selected from the group consisting of: SEQ ID NOs. 1-6.

Utility

In a preferred embodiment, the antibodies of the present invention are human, humanized or chimeric monoclonal antibodies appropriate for administration to humans. These antibodies can be used alone or as a component in a mixture with other antibodies or other pharmaceutical agents to treat cancers or image cancerous tissues.

Regardless of whether the present antibodies are used for therapy or diagnosis, they can be administered orally, parenterally, subcutaneously, intravenously, intramuscularly, intraperitoneally, by intranasal instillation, by intracavitary or intravesical instillation, intraocularly, intramierially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the biological agent, such as an antibody or binding portion thereof, of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The antibodies of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the antibodies of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically from about 0.1 mg/kg to about 100 mg/kg of the patient's body weight. Preferably, the dosage administered to a patient is between about 0.1 mg/kg and about 20 mg/kg of the patient's body weight, more preferably about 1 mg/kg to about 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

In a preferred aspect, the patient to be treated with a monoclonal antibody of the invention is first tested for p-Akt positivity, e.g., the level of expression of P-Akt by the patient's disease is determined. Techniques known to those of skill in the art can be used for measuring p-Akt activity in a patient sample. For example, p-Akt expression can be assayed, for example, by immunoassays including, but not limited to, competitive and non-competitive assay systems using techniques such as western blots, immunohistochemistry (IHC), radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the level of expression of p-Akt is measured by IHC techniques using either an antibody of the resent invention or a commercial anti-p-Akt antibody, such as those available from Cell Signaling Technologies.

The present antibodies may be utilized to detect cancerous tissues in vivo or in an in vitro diagnostic test. This is achieved by labeling the antibody or binding fragment thereof, administering the labeled agent to a mammal, and then imaging the mammal.

Examples of labels useful for diagnostic or prognostic applications in accordance with the present invention are radiolabels, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The antibody can be labeled with such reagents using techniques known in the mi. For example, see Wensel and Meares, Radioimmunoimaging and Radioimmunotherapy, Elsevier, New York (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", Meth. Enzymol., 121: 802 816 (1986), which is hereby incorporated by reference.

A radiolabeled antibody or fragment of this invention can be used for in vitro diagnostic tests. The specific activity of a tagged biological agent, such as a tagged antibody, binding portion thereof, probe, or ligand, depends upon the half-life, the isotopic purity of the radioactive label, and how the label is incorporated into the biological agent. In immunoassay tests, the higher the specific activity, in general, the better the sensitivity.

Procedures for labeling antibodies and other biological agents with radioactive isotopes are generally known in the art. Tritium labeling procedures are described in U.S. Pat. No. 4,302,438, which is hereby incorporated by reference. Procedures especially adapted for murine monoclonal antibodies are described by Goding, J. W. (supra, pp 124 126) and the references cited therein, which are hereby incorporated by reference. Other procedures for iodinating biological agents, such as antibodies, binding portions thereof, probes, or ligands, are described by Hunter and Greenwood, Nature, 144:945 (1962), David et al., Biochemistry, 13:1014 1021 (1974), and U.S. Pat. Nos. 3,867,517 and 4,376,110, which are hereby incorporated by reference. Procedures for iodinating biological agents are described by Greenwood, F. et al., Biochem. J., 89:114 123 (1963); Marchalonis, J., Biochem. J., 113:299 305 (1969); and Morrison, M. et al., Immunochemistry, 289 297 (1971), which are hereby incorporated by reference. Procedures for technicium labeling are described by Rhodes, B. et al. in Burchiel, S. et al. (eds.), Tumor Imaging: The Radioimmunochemical Detection of Cancer, New York: Masson 111 123 (1982) and the references cited therein, which are hereby incorporated by reference. Procedures suitable for labeling biological agents also are described by Hnatowich, D. J. et al., J Immul. Methods, 65:147 157 (1983), Hnatowich, D. et al., J. Applied Radiation, 35:554 557 (1984), and Buckley, R. G. et al., F.E.B.S., 166:202 204 (1984), which are hereby incorporated by reference.

In the case of a radio labeled antibody, the antibody or fragment thereof is administered to the patient, is localized to the tumor bearing the antigen with which the biological agent reacts, and is detected or "imaged" in vivo using known techniques such as radionuclear scanning using e.g., a gamma camera or emission tomography. See e.g., R. Bradwell et al., "Developments in Antibody Imaging", Monoclonal Antibodies for Cancer Detection and Therapy, R. W. Baldwin et al., (eds.), pp. 65 85 (Academic Press 1985), which is hereby incorporated by reference. Alternatively, a positron emission transaxial tomography scanner, such as designated Pet VI located at Brookhaven National Laboratory, can be used where the radiolabel emits positrons.

Fluorophore and chromophore labeled antibodies or fragments thereof can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, Science, 162:526 (1968) and Brand, L. et al., Annual Review of Biochemistry, 41:843 868 (1972), which are hereby incorporated by reference. The biological agents can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies or fragments thereof can be labeled with fluorochromes or chromophores by the procedures described by Goding, J. (supra, pp 208 249). The antibody or fragment can be labeled with an indicating group containing the NMR-active fluorine atom, or a plurality of such atoms inasmuch as (i) substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described by Pykett, *Scientific American,* 246:78 88 (1982), which is hereby incorporated by reference, to locate and image cancerous tissues.

The antibody or fragment can also be utilized to kill or ablate cancerous cells in vivo. This involves using the present antibodies or fragments thereof by themselves or with a cytotoxic drug to which the antibody or fragment of the present invention are bound. This involves administering the present antibodies or fragments thereof bonded to a cytotoxic drug to a mammal requiring such treatment.

The antibody or fragment of the present invention may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy a-emitters.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, a-sacrin, certain *Aleurites fordii* proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the present antibodies or fragments thereof with the cytotoxic agents have been previously described. Procedures for conjugating chlorambucil with antibodies are described by Flechner, I., *European Journal of Cancer,* 9:741 745 (1973); Ghose, T. et al., *British Medical Journal,* 3:495 499 (1972); and Szekerke, M., et al., *Neoplasma,* 19:211 215 (1972), which are hereby incorporated by reference. Procedures for conjugating daunomycin and adriamycin to antibodies are described by Hurwitz, E. et al., *Cancer Research,* 35:1175 1181 (1975) and Amon, R. et al. *Cancer Surveys,* 20 1:429 449 (1982), which are hereby incorporated by reference. Procedures for preparing antibody-ricin conjugates are described in U.S. Pat. No. 4,414,148 and by Osawa, T., et al. *Cancer Surveys,* 1:373 388 (1982) and the references cited therein, which are hereby incorporated by reference. Coupling procedures as also described in EP 86309516.2, which is hereby incorporated by reference.

Alternatively, the present antibodies or fragments thereof can be coupled to high energy radiation emitters, for example, a radioisotope, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy,* R. W. Baldwin et al. (eds.), pp 303 316 (Academic Press 1985), which is hereby incorporated by reference. Other suitable radioisotopes include α-emitters, and α-emitters. Radiotherapy is expected to be particularly effective, because prostate epithelial cells and vascular endothelial cells within cancers are relatively radiosensitive.

Where the present antibodies or fragments thereof are used alone to kill or ablate cancerous cells or prostate epithelial cells, such killing or ablation can be effected by initiating endogenous host immune functions, such as complement-mediated or antibody-dependent cellular cytotoxicity.

The antibodies or fragments thereof of the present invention can be used and sold together with equipment, as a kit, to detect the particular label.

The antibodies or fragments thereof of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method of killing or ablating which involves using the antibody or fragment for prophylaxis. For example, these materials can be used to prevent or delay development or progression of cancers.

The Examples below sets forth the results of a preclinical evaluation of a monoclonal antibody produced according to the present invention. The results obtained indicate that the monoclonal antibody is effective as an anti-tumor agent. The monoclonal antibody of the present invention was able to mediate different biological responses in vitro, including inhibition of phospho-AKT-dependent cell growth, as well as reduce tumor growth via apoptosis in mice implanted with human gastrointestinal stromal tumor (GIST) cells, while exhibiting no adverse effects in murine toxicology models.

EXAMPLES

Example 1

Three murine monoclonal antibodies were prepared by immunizing SCID mice with synthetic phospho-Akt peptides, and establishing hybridomas according to the general procedure described by Iyer et al., *Ind. J Med. Res.,* 123: 651-564 (2006). Each mouse was immunized with two peptides as follows.

| Mouse/Hybridoma | Peptides |
| --- | --- |
| A | SEQ ID NOs. 1 and 2 |
| B | SEQ ID NOs. 3 and 4 |
| C | SEQ ID NOs. 5 and 6 |

The three monoclonal antibodies were tested by Western blot and Western dot blot to determine their reactivity and specificity with a p-Akt. The results of the Western blot (FIG. 1A) show that the three monoclonal antibodies have substantially the same specificity for p-Akt protein. The results of the Western dot blot (FIG. 1B) show that all three monoclonal antibodies have substantially the same reactivity with a p-Akt protein at varying dilutions.

Figure 2:
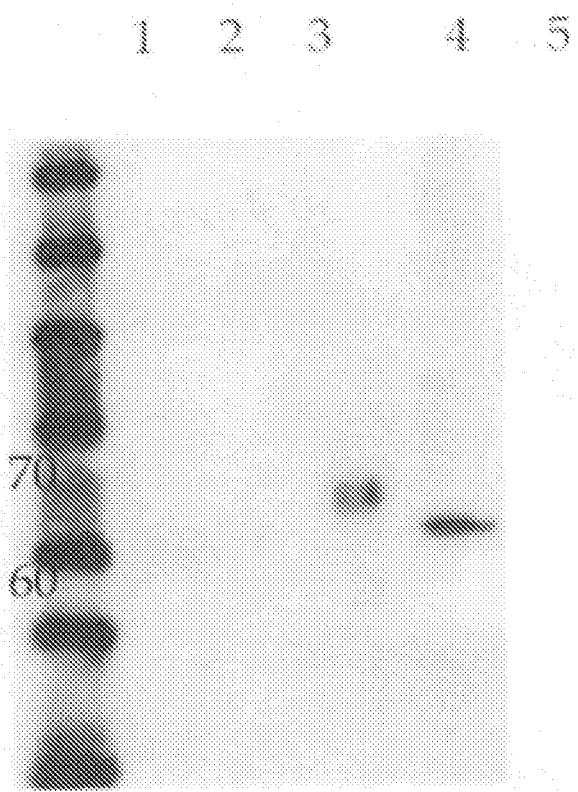
FIG. 2 is a Western blot of an anti-p-Akt antibody of the invention (Lane 4) and commercial anti-p-Akt substrate antibody (Lane 5). Lane 1 contains molecular weight markers.

The monoclonal antibody produced by hybridoma C, designated NU-1001-41, was used in the following studies, although the antibodies A and B would be expected to achieve the same results. NU-1001-41 has a molecular weight of about 63 KDa, and an Isotype of lgA/IgM. FIG. 2 shows a Western Blot showing the MW of NU-1001-41 using a commercial non-human p-Akt substrate monoclonal antibody for comparison (Cell Signaling Technology, Catalog No. #9614).

Xenografts of GIST tumors were grown by injecting nude mice with cells from a primary tumor cell line. The GIST882 cell line was used for this purpose because GIST882 cells overexpress pAkt. When injected into mice or other host animal, the GIST 882 cells quickly form tumors in the animal. It is believed that the GIST cells grow well because AKT is phosphorylated and p-Akt is overexpressed in these cells and protects against cell death by inhibiting apoptosis. NU-1001-41 targets and binds p-Akt, thereby blocking the phosphorylation step, which in turn drives the cells into an apoptotic state. The GIST882 human GIST cell line was obtained from Jonathan Fletcher, MD (Brigham and Women's Hospital, Boston Mass.).

Female nude mice (nu/nu) between 5 and 6 weeks of age weighing approximately 20 g were obtained from Harlan, Inc. (Madison, Wis.). On day 0, animals were injected subcutaneously (s.c.) with 100 µl of a cell suspension containing 5×106 cells harvested from in vitro culture. On day 1, mice were randomized into their respective groups and treated with the various antibodies. All of the groups contained 10 mice and the animals were ear-tagged and followed individually throughout the experiment. NU-1001-41 antibody was administered intravenously (i.v) three times a week for 4 weeks at doses of 2.86, 8.55 or 17.1 mg/kg of NU-1001-41. As a negative control, normal murine IgG was administered i.v. three times a week for 4 weeks. As an additional negative control, phosphate buffered saline (PBS) was given at a volume of 200) µl/mouse on the same schedule as the treatment groups. Mice were weighed twice weekly, starting on day 1. Beginning on day 5, tumor measurements were taken twice weekly. Tumor measurements were converted to mm3 tumor volume by the standard formula, (W2×L)/2, where L and W are the major and minor diameters of the tumor expressed in millimeters, respectively.

Samples were collected from all of the mice 30 days after intraperitoneal injection of 5×106 late passage GIST882 cells. In mice injected with normal murine IgG and PBS, multiple tumors were present throughout the peritoneal cavity, covering the body wall. Mice treated with the NU-1001-41 antibody evidenced a marked decrease of tumor volume and burden.

After the intravenous infusion, all physical observations, clinical chemistries, body weights, food consumption, gross pathology and histopathologies were considered to be normal. The only exception was a dose-related increase in spleen size and in the number of lymphoid follicles in the white pulp. Hyperplasia of the lymphoid zone of the spleen is a known effect of injection of antigenic or immune stimulant and considered to be due to foreign proteins. Other lymphoid tissues, including the mesenteric and mediastinal lymph nodes and the thymus, did not show any apparent NU-1001-41-related alterations in lymphocyte populations. The splenic changes observed in the animals sacrificed immediately post-infusion were not seen in the 28-day recovery animals. The size and number of splenic lymphoid follicles were similar in control and NU-1001-41-treated animals, indicating recovery from any lymphocyte stimulation caused by the antibody. In fact, the number and size of lymphoid follicles in the control recovery animals was similar to that seen in most of the test antibody-treated animals at the end of dosing, suggesting that the lymphoid stimulation seen at the end of dosing was within the normal physiological range. As no adverse events were observed, the no observed adverse effect level was estimated to be greater than 16.8 mg/kg, over 28 day. No drug-related pathologic changes were observed.

Mouse GIST 882 Metastatic Tumor in Lung

NU-1001-41 also was found to inhibit pulmonary metastasis in dose-dependent SCID GIST882 mice systemically disseminated with GIST882 cells.

To explore the potential anti-tumor effect of targeting phospho-Akt in vivo, and assuming that effector functions in mouse are better mediated by a murine antibody rather than by its humanized version, the murine NU-1001-41 antibody was used to treat nude mice implanted with GIST882 cells according to the procedure described above. Animals were treated with vehicle, isotype-matched normal murine IgG or NU-1001-41 following a regimen consisting of 0.1 mg/dose administered three times a week for 4 weeks, while monitoring for tumor volumes twice a week for up to 2 months.

A significant reduction of tumor growth (approx. 62%) was observed with the NU-1001-41 treatment (0.1 mg/dose) compared to an equivalent dose of the normal IgG control ($P<0.05$). Higher doses of NU-1001-41 led to an overall increase in tumor suppression. All treated animals were tested for p-Akt positivity by IHC using an anti-p-Akt antibody from Cell Signaling Technology (CS #9614), and confirmed to be p-Akt positive.

Example 2

Immunohistochemistry

Immunohistochemical (IHC) staining techniques were used for the visualization of tissue (cell) antigens, specifically, p-Akt and substrates of p-Akt that contain a peptide sequence recognized by NU-1001-41. These techniques are based on the immunoreactivity and specificity of antibodies, and the chemical properties of enzymes or enzyme complexes which react with colorless substrate-chromogens to produce a colored end product. IHC staining techniques include direct and indirect methods, either of which can be used.

In the direct method, the chromogen is conjugated directly to an antibody with known antigenic specificity (primary antibody). This technique allows the visualization of tissue antigens using standard light microscopy. The indirect method is a two-step method in which enzyme-labeled secondary antibodies react with the antigen-bound primary antibody. Enzyme pairs which can be used in the indirect method include peroxidase-antiperoxidase (PAP) and avidin-biotin. In the present experiment, the indirect method using an avidin-biotin complex (ABC) was employed, in which a biotinylated secondary antibody forms a complex with peroxidase-conjugated streptavidin molecules. Endogenous peroxidase activity was quenched by the addition of 3% hydrogen peroxide. The specimens then were incubated with the primary antibody, the NU-1001-41 antibody, followed by sequential incubations with the biotinylated secondary link antibody (containing antianti-mouse immunoglobulins) and peroxidase labeled streptavidin. The primary antibody-secondary antibody-avidin enzyme complex then was visualized utilizing a substrate-chromogen that produces a brown pigment at the antigen site that is visible by light microscopy.

Tissue Microarrays

The IHC technique described above was used to interrogate biopsied tissues, including GIST tumor tissues and various positive and negative control tissues. The tissues were arrayed on slides forming tissue microarrays (TMAs) so that all of the tissues were subjected to the same reagents and conditions. The TMAs used for this study are outlined in Table A.

TABLE A

| | |
|---|---|
| Fixation: | Formalin Fixed, Paraffin Embedded (FFPE) |
| Construction: | Holes were created in a recipient paraffin block that are then filled with tissue cores acquired from selected donor blocks of tissue. These tissue cores are punched with a thin walled, sharpened borer. An X-Y precision guide allows for the orderly placement of these tissue samples in an array format onto a glass slide. |
| Presentation: | Sections (4 microns) are cut from the recipient block and are mounted on positively charged glass microslides. Individual elements are 0.6 mm in diameter, spaced 0.2 mm apart. |
| Elements: | The TMAs used in this experiment included the following tissues: A TMA was constructed with Xenograft GIST882 tumor tissue (from the xenograft mice described above, prior to treatment with the NU-1001-41 antibody) and cardiac tissues obtained from mouse and human sources. A TMA was constructed (Normal Control Array) containing the following human normal (noon-cancerous) control tissues: adrenal gland, parotid gland, breast, thyroid gland, lung, stomach, esophagus, kidney, colon, prostate, muscle, liver, and lymph node. Two samples of each of the tissues were used. |
| Specificity: | The TMA was designed for use with specialty staining and immunohistochemical methods for gene expression screening purposes by using monoclonal and polyclonal antibodies over a wide range of characterized tissue types. |
| Data: | Accompanying each array is an array locator map and spreadsheet containing patient diagnostic, histologic and demographic data for each element. |

The TMAs were subjected to the following IHC procedure:

1) Perform heat-induced epitope retrieval (HIER) using 10 mM Citrate buffer solution, pH 6.0.
   a. Place deparaffinized and rehydrated sections in a slide staining rack.
   b. Place the rack in a microwaveable pressure cooker. Add 750 ml of 10 mM citrate buffer pH 6.0 to cover the slides.
   c. Place the covered pressure cooker in the microwave on high power for 15 minutes.
   d. Remove pressure cooker from the microwave and cool until the pressure indicator drops and the cover can be safely removed.
   e. Allow slides to cool to room temperature. (approx. 30 min.).
   f. Proceed with the immunohistochemical staining.
2) Treat slides with 3% $H_2O_{22}$ for 10 min. at RT to quench endogenous peroxidase activity.
3) Gently rinse slides with phosphate buffered saline (PBS).
4) Apply primary antibody*, at the predetermined dilution for 30 min at RT. (apply normal mouse or rabbit serum 2 1:750 dilution to negative control slides).
5) Gently rinse slides with phosphate buffered saline (PBS).
6) Apply secondary biotinylated link antibody** for 30 min at RT.
7) Gently rinse slides with phosphate buffered saline (PBS).
8) Treat with streptavidin-HRP*** (streptavidin conjugated to horseradish peroxidase) 4 for 30 min at RT.
9) Gently rinse slides with phosphate buffered saline (PBS).
10) Treat with substrate/chromogen**** 5 for 10 min at RT.
11) Gently rinse slides with distilled water.
12) Counterstain in Hematoxylin for 1 min.
13) Wash slides in running water for 2 min.
14) Dehydrate, clear and mount cover glass.

*Primary antibody: the NU-1001-41 monoclonal antibody

**Secondary antibody: biotinylated anti-chicken and anti-mouse immunoglobulins in phosphate buffered saline (PBS), containing carrier protein and 15 mM sodium azide.

*** Streptavidin-HRP in PBS containing carrier protein and anti-microbial agents from Ventana

****Substrate-Chromogen (substrate-imidazole-HCl buffer pH 7.5 containing H202 and antimicrobial agents. DAB-3,3'-diaminobenzidine in chromogen solution) from Ventana The slides were screened to determine the optimal working dilution. Pretreatment with HIER provided strong specific staining with little or no background.

Staining was scored as described by Signoretti et al., *J Natl. Cancer Instit.*, 92(23):1918-25 (2000) and Gu et al., *Oncogene*, 19:1288-96 (2000). Scoring was done on a 0-3+ scale, with 0=no staining, and trace (tr) being less than 1+ but greater than 0. Grades of 1+ to 3+ represent increased intensity of staining with 3+ being strong, dark brown staining Scoring criteria also were based on total percentage of staining 0=0%, 1=less than 25%, 2=25-50% and 3=greater than 50%. The percent positivity and the intensity of staining for both nuclear and cytoplasmic as well as sub-cellular components were analyzed. Both the intensity and percentage positive scores were multiplied to produce one number 0-9. A score of 3+ was determined from known expression of the antigen from the positive controls either breast adenocarcinoma and/or LNCAP cells. The results for the xenograft tissues are shown in Table B.

TABLE B

IHC Results for Xenograft Mice

| Xenografts (Dosage of NU-1001-41) | Cyto % Positive | Cyto Intensity | Cyto Total Score | Nuclear % Positive | Nuclear Intensity | Nuclear Total Score |
|---|---|---|---|---|---|---|
| GIST882 (2.86 mg/kg) | 3 | 3 | 9 | 3 | 2 | 6 |
| GIST882 (2.86 mg/kg) | 3 | 1 | 3 | 3 | 3 | 9 |

TABLE B-continued

IHC Results for Xenograft Mice

| Xenografts (Dosage of NU-1001-41) | Cyto % Positive | Cyto Intensity | Cyto Total Score | Nuclear % Positive | Nuclear Intensity | Nuclear Total Score |
|---|---|---|---|---|---|---|
| GIST882 (2.86 mg/kg) | 3 | 1 | 3 | 3 | 3 | 9 |
| GIST882 (8.55 mg/kg) | 3 | 2 | 6 | 3 | 2 | 6 |
| GIST882 (8.55 mg/kg) | 3 | 1 | 3 | 3 | 2 | 6 |
| GIST882 (8.55 mg/kg) | 3 | 1 | 3 | 3 | 2 | 6 |
| GIST882 (8.55 mg/kg) | 3 | 2 | 6 | 3 | 2 | 6 |
| GIST882 (8.55 mg/kg) | 3 | 2 | 6 | 3 | 2 | 6 |
| GIST882 (17.1 mg/kg) | 3 | 2 | 6 | 3 | 3 | 9 |
| GIST882 (17.1 mg/kg) | 3 | 3 | 9 | 3 | 3 | 9 |
| GIST882 (17.1 mg/kg) | 3 | 1 | 3 | 3 | 2 | 6 |
| GIST882 (17.1 mg/kg) | 3 | 1 | 3 | 3 | 2 | 6 |
| GIST882 (17.1 mg/kg) | 3 | 1 | 3 | 3 | 2 | 6 |
| GIST882 (17.1 mg/kg) | 3 | 1 | 3 | 3 | 2 | 6 |

Table B shows that the GIST xenograft tissue prior to treatment with NU-1001-41 stained strongly positive for p-Akt using the NU-1001-41 antibody.

All runs were grouped by antibody and tissue arrays which ensures that the runs are normalized, i.e., meaning that all if the tissue arrays are stained under the same conditions with the same antibody on the same run.

In order to detect possible cross-reactivity, NU-1001-41 was applied to a panel of normal human tissues (the Normal Control Array described above). TMAs containing these tissues were prepared and stained with the NU-1001-41 antibody as described above. The results are shown in Table C below.

TABLE C

| Normal Tissue Type | Cyto Score | Underlying Disease* | Sex | Age |
|---|---|---|---|---|
| Breast | 1 | None | f | 83 |
| Breast | 1 | None | f | 59 |
| Parotid | 0 | None | f | 74 |
| Parotid | 0 | None | f | 61 |
| Thyroid | 0 | None | f | 68 |
| Lung | 1 | None | m | 78 |
| Lung | 1 | None | m | 56 |
| Stomach | 1 | None | m | 68 |
| Stomach | 1 | None | m | 60 |
| Esophagus | 1 | None | f | 71 |
| Esophagus | 1 | None | f | 69 |
| Kidney | 1 | None | f | 51 |
| Adrenal | 0 | None | m | 56 |
| Normal Colon | 3 | Colon cancer, adenocarcinoma | m | 70 |
| Normal Colon | 3 | Colon cancer, adenocarcinoma | f | 71 |
| Normal Colon | 2 | Colon cancer, adenocarcinoma | m | 65 |
| Normal Colon | 1 | Colon cancer, adenocarcinoma | m | 79 |
| Normal Colon | 1 | None | m | 74 |
| Normal Colon | 1 | None | f | 81 |
| Normal Colon | 1 | None | m | 78 |
| Prostate | 3 | Prostate cancer, adenocarcinoma | m | 85 |
| Prostate | 2 | Prostate cancer, adenocarcinoma | m | 85 |
| Prostate | 2 | Prostate cancer, adenocarcinoma | m | 77 |
| Prostate | 1 | None | m | 71 |
| Prostate | 1 | None | m | 70 |
| Prostate | 1 | None | m | 60 |
| Prostate | 1 | Benign prostate hyperplasia | m | 73 |
| Normal skeletal muscle | 2 | Breast cancer | f | 79 |
| Normal skeletal muscle | 2, 3 | Breast cancer | f | 57 |
| Normal kidney, cortex | 0 | Renal pelvis TCC | m | 78 |
| Normal Kidney, cortex | 0 | Renal pelvis TCC | m | 87 |
| Normal liver | 0 | splenomegaly | f | 71 |
| Normal liver | 0 | Hodgkin disease | f | 26 |
| Normal lymph node | 2 | Colon cancer | m | 60 |
| Normal lymph node | 4 | Colon cancer | f | 76 |
| Normal prostate | 2 | Prostate cancer | m | |
| Normal prostate | 1 | BPH | m | 68 |
| Normal thyroid | 0 | Thyroid adenoma | f | 47 |
| Normal thyroid | 0 | Thyroid adenoma | m | 26 |

*Normal tissue derived from patients having underlying disease was disease-free or margin tissue.

The low scores show that the binding profile of NU-1001-41 has very limited reactivity with normal tissues. The results in Table C show that the NU-1001-41 antibody infrequently stained the stomach epithelium, epithelium of the esophagus, and duct epithelium of the pancreas in both normal human and murine tissues. Higher scores, such as that found in the normal lymph node derived from a colon cancer patient, are thought to be artifacts related to the presence of undetected disease in the marginal tissue.

The results set forth above demonstrate that the NU-1001-41 antibody is capable of reducing tumor growth in a xenograft model employing GIST882 human GIST cells. The NU-1001-41 antibody mediates apoptotic activity on tumor cells expressing p-Akt. The activity of the NU-1001-41 antibody fits the multimodal profile of a naked monoclonal antibody that exerts pharmacological activity against tumor cells.

Example 3

Cardiac Tissue Staining in Murine Models

Cardiac Toxicity

In order to ascertain whether the NU-1001-41 antibody TMAs were constructed according to the procedure described in Example 1 containing murine female cardiac tissue. The TMAs were stained with the NU-1001-41 antibody using the IHC protocol described in Example 1. The results showed negative staining in the cardiac tissue with no significant binding indicating no significant cardiac toxicity seen.

Example 4

The NU-1001-41 monoclonal antibody was tested in xenograft mice that had been implanted with the GIST882 cells as described in Example 1. CDF male mice weighing 18 to 25 g received intraperitoneal injections of GIST882 ascites tumor cells 20 days prior to day 0. After twenty days, GIST tumors developed in all mice. Mice bearing the GIST tumors then were treated with NU-1001-41 alone, and in combination with three chemotherapeutic agents: methotrexate, Cytoxan and 5-fluorouracil, and the effect of the tumors was observed.

The chart below shows a comparison of the influence dose schedules and constant dose schedules of NU-1001-41 monoclonal antibody on survival time. The survival time of untreated control mice was about 10 to 11 days. There were 5 mice per dose group. The following abbreviations are used for the dose response: R=Responder, NR=Non Responder, DE—Died Early.

"Responder" indicates that the mice responded positively to treatment, either with a longer survival time compared to the untreated mice, a reduction or disappearance of the tumor (determined by palpation) or both.

| NU-1001-41 Antibody without Additional Chemotherapeutics | | | | | | | | | | | | |
|---|---|---|---|---|---|---|---|---|---|---|---|---|
| Daily dose of NU-1001-41 (µl/kg) from day 1 to | NU-1001-41 (days) Initial dose of NU-1001-41 on day 1 (µ/kg) | | | | | | | | | | | |
| death or improvement | Day 0 | Day 1 | Day 2 | Day 3 | Day 4 | Day 5 | Day 6 | Day 7 | Day 8 | Day 9 | Day 10 | Day 11 |
| 2-4 | 0 | 2 | 2 | 2 | 2.5 | 2.5 (NR) | 2.7 (NR) | 2.9 (NR) | 3 (NR) | 3 (NR) | 3.8 (NR) | 4 (NR) |
| 5-6 | 0 | 5 | 5 | 5 | 5 | 5.5 | 5.5 | 6 (NR) | 6 (NR) | 6 (NR) | 6 (NR) | 6 (NR) |
| 7-8.4 | 0 | 7 | 7.2 | 7.2 | 7.2 | 7.4 | 7.4 | 7.8 (NR) | 8 (NR) | 8 (NR) | 8 (NR) | 8.4 (NR) |
| 9.3 | 0 | 9.3 | 9.3 | 9.3 (NR) | 9.3 (NR) | 9.3 (NR) | 9.3 (NR) | 9.3 (NR) | 9.3 (NR) | 9.3 (NR) | 9.3 (NR) | DE |
| 9.8 | 0 | 9.8 | 9.8 (R) | 9.8 (R) | 9.8 (R) | 9.8 (R) | 9.8 (R) | 9.8 (R) | 9.8 (R) | 9.8 (R) | 9.8 (R) | 9.8 (R) |
| 10 | 0 | 10 | 10 | DE (TOX) | | | | | | | | |

As shown in the chart, the mice receiving a dose of the NU-1001-41 antibody of 9.3 µl/kg responded to the treatment on day 8, and the mice receiving a dose of 9.8 µl/kg responded positively on day 2 of treatment.

| NU-1001-41 with 5-fluoro uracil (5-FU) | | | | | | | | | | | | |
|---|---|---|---|---|---|---|---|---|---|---|---|---|
| Daily dose of NU-1001-41 below (µl/kg) Dose of 5-FU | NU-1001-41 (days) Initial dose of NU-1001-41 on day 1 (mg/kg) | | | | | | | | | | | |
| (µl/kg) in parentheses | Day 0 | Day 1 | Day 2 | Day 3 | Day 4 | Day 5 | Day 6 | Day 7 | Day 8 | Day 9 | Day 10 | Day 11 |
| 2-4 | 0 | 2 (1) | 2 (1) | 2 (1) | 2.5 (1) (NR) | 2.5 (1) (NR) | 2.7 (1) (NR) | 2.9 (1) (NR) | 3 (1) (NR) | 3 (1) (NR) | 3.8 (1) (NR) | 4 (1) (NR) |
| 5-6 | 0 | 5 (2.5) | 5 (2.5) | 5 (2.5) | 5 (2.5) | 5.5 (2.5) | 5.5 (2.5) | 6 (2.5) (NR) | 6 (2.5) (NR) | 6 (2.5) (NR) | 6 (2.5) (NR) | 6 (2.5) (NR) |
| 7-8.4 | 0 | 7 (2.5) | 7 (2.5) | 7.2 (2.5) | 7.2 (2.5) | 7.4 (2.5) | 7.4 (3.5) | 7.8 (3.5) (NR) | 8 (3.5) (NR) | 8 (3.5) (NR) | 8 (3.5) (NR) | 8.4 (3.5) (NR) |
| 9.3 | 0 | 9.3 (3.5) (0) | 9.3 (3.5) | 9.3 (3.5) (NR) | 9.3 (3.5) (NR) | 9.3 (3.5) (NR) | 9.3 (3.5) (NR) | 9.3 (3.5) (NR) | 9.3 (3.5) (R) | 9.3 (3.5) (R) | 9.3 (3.5) (R) | 9.3 (3.5) (R) |
| 9.8 | 0 | 9.8 (6) | 9.8 (6) (R) | 9.8 (6) (R) | 9.8 (6) (R) | 9.8 (6) (R) | 9.8 (6) (R) | 9.8 (6) (R) | 9.8 (6) (R) | 9.8 (6) (R) | 9.8 (6) (R) | 9.8 (6) (R) |
| 10 | 0 | 10 (7) | DE | DE | | | | | | | | |

As shown in the chart, the mice receiving a dose of the NU-1001-41 antibody of 9.3 µl/kg and 3.5 µl/kg of 5-FU responded to the treatment on day 8, and the mice receiving a dose of 9.8 µl/kg of NU-1001-41 antibody and 6 µl/kg of 5-FU responded positively on day 2 of treatment.

| NU-1001-41 with Methotrexate (MTX) | | | | | | | | | | | | |
|---|---|---|---|---|---|---|---|---|---|---|---|---|
| Daily dose of NU-1001-41 below (μl/kg) Dose of 5-MTX (μl/kg) in parentheses | NU-1001-41 (days) Initial dose of NU-1001-41 on day 1 (mg/kg) | | | | | | | | | | | |
| | Day 0 | Day 1 | Day 2 | Day 3 | Day 4 | Day 5 | Day 6 | Day 7 | Day 8 | Day 9 | Day 10 | Day 11 |
| 2-4 | 0 | 2 (3) | 2 (3) | 2 (3) | 2.5 (3) | 2.5 (3) (NR) | 2.7 (3) (NR) | 2.9 (3) (NR) | 3 (3) (NR) | 3 (3) (NR) | 3.8 (3) (NR) | 4 (3) (NR) |
| 5-6 | 0 | 5 (4.2) | 5 (4.2) | 5 (4.2) | 5 (4.2) | 5.5 (4.2) | 5.5 (4.2) | 6 (4.2) (NR) | 6 (4.2) (NR) | 6 (4.2) (NR) | 6 (4.2) (NR) | 6 (4.2) (NR) |
| 7-8.4 | 0 | 7 (4.2) | 7 (4.2) | 7.2 (4.2) | 7.2 (4.2) | 7.4 (4.2) | 7.4 (5.6) | 7.8 (5.6) (NR) | 8 (5.6) (NR) | 8 (5.6) (NR) | 8 (5.6) (NR) | 8.4 (5.6) (NR) |
| 9.3 | 0 | 9.3 (5.6) | 9.3 (5.6) | 9.3 (5.6) (NR) | 9.3 (5.6) (NR) | 9.3 (5.6) (NR) | 9.3 (5.6) (NR) | 9.3 (5.6) (NR) | 9.3 (5.6) (R) | 9.3 (5.6) (R) | 9.3 (5.6) (R) | 9.3 (5.6) (R) |
| 9.8 | 0 | 9.8 (6) | 9.8 (6) (R) | 9.8 (6) (R) | 9.8 (6) (R) | 9.8 (6) (R) | DE | | | | | |
| 10 | 0 | 10 (7) | DE | | | | | | | | | |

As shown in the chart, the mice receiving a dose of the NU-1001-41 antibody of 9.3 μl/kg and 5.6 μl/kg of MTX responded to the treatment on day 8, and the mice receiving a dose of 9.8 μl/kg of NU-1001-41 antibody and 6 μl/kg of MTX responded positively on day 2 of treatment.

| NU-1001-41 with Cytoxan (CTX) | | | | | | | | | | | | |
|---|---|---|---|---|---|---|---|---|---|---|---|---|
| Daily dose of NU-1001-41 below (μl/kg) Dose of CTX (μl/kg) in parentheses | Day 0 | Day 1 | Day 2 | Day 3 | Day 4 | Day 5 | Day 6 | Day 7 | Day 8 | Day 9 | Day 10 | Day 11 |
| 2-4 | 0 | 2 (4.4) | 2 (4.4) | 2 (4.4) | 2.5 (4.4) | 2.5 (4.4) (NR) | 2.7 (4.4) (NR) | 2.9 (4.4) (NR) | 4 (4.4) (NR) | 4 (4.4) (NR) | 4 (4.4) (NR) | 4 (4.4) (NR) |
| 5-6 | 0 | 5 (5.3) | 5 (5.3) | 5 (5.3) | 5 (5.3) | 5.5 (5.3) | 5.5 (5.3) | 6 (5.3) (NR) | 6 (5.3) (NR) | DE | | |
| 7-8.4 | 0 | 7 (5.6) | 7 (5.6) | 7.2 (5.6) | 7.2 (5.6) | 7.4 (5.6) | 7.4 (5.6) | 7.8 (5.6) (NR) | 8 (5.6) (NR) | 8 (5.6) (NR) | 8 (5.6) (NR) | 8.4 (5.6) (NR) |
| 9.3 | 0 | 9.3 (6.7) | 9.3 (6.7) | 9.3 (6.7) (NR) | 9.3 (6.7) (NR) | 9.3 (6.7) (NR) | 9.3 (6.7) (NR) | 9.3 (6.7) (NR) | 9.3 (6.7) (R) | 9.3 (6.7) (R) | 9.3 (6.7) (R) | 9.3 (6.7) (R) |
| 9.8 | 0 | 9.8 (7.9) | 9.8 (7.9) (R) | 9.8 (7.9) (R) | DE | | | | | | | |
| 10 | 0 | 10 (9) | DE | | | | | | | | | |

As shown in the chart, the mice receiving a dose of the NU-1001-41 antibody of 9.3 μl/kg and 6.7 μl/kg of CTX responded to the treatment on day 8, and the mice receiving a dose of 9.8 μl/kg of NU-1001-41 antibody and 7.9 μl/kg of CTX responded positively on day 2 of treatment.

MTX, 5-FU and Cytoxan alone historically do not work well for GIST tumors. As these chemo products work to kill cells, they work so slowly that the rapidly growing GIST tumor typically overcomes their effectiveness. All three drugs can induce apoptosis on their own but do so very slowly, they do not act upon the p-Akt pathway. By using NU-1 001-41 and driving the tumor into apoptosis, the chemo drugs take effect much more quickly. It is believed that both together they would have a good outcome. This should be confirmed by larger animal studies. The effectiveness of these drugs together with the NU-1 001-41 antibody can be measured by showing a reduction in tumor size and tumor burden, as shown in Table D below.

TABLE D

GIST 882 xenograft tumor burden comparison model

| Mouse Sampling | NU-1001-41 Alone (9.3 mg/kg) | NU-1001-41 (9.3 mg/kg) w/MTX (5.6 mg/kg) | NU-1001-41 (9.3 mg/kg) w/5 FU (3.5 mg/kg) | NU-1001-41 (9.3 mg/kg) w/CTX (6.7 mg/kg) |
|---|---|---|---|---|
| 1 | .5 cm | 2 cm | 1.5 cm | 2 cm |
| 2 | .5 cm | 1.5 cm | 1.5 cm | 2 cm |
| 3 | .5 cm | 1.5 cm | 1.5 cm | 1.5 cm |
| 4 | Min | 2 cm | 1.5 cm | 1.5 cm |
| 5 | Min | 1.5 cm | 1.0 cm | 2 cm |

This study used a sampling of 5 animals from each category. Tumor burden was measured after treatment and compared to tumors in untreated animals. The numbers indicated in the boxes show the amount of the decrease of tumor burden. The average tumor size was 6 cm. These results show that the decrease in the size of the tumor was significantly greater for mice treated with a combination of the antibody and MTX, CTX or 5-FU than with the antibody alone.

Example 5

The ability of the NU-1001-41 monoclonal antibody to inhibit p-AKT activity in glioblastoma was tested in glioblastoma cells and in xenograft tumors from mice that had been implanted with glioblastoma cells (SF-295). The SF-295 cell line was obtained from the National Cancer Institute (Frederick, Md.).

P-Akt Inhibition in Glioblastoma Xenograft Tissue

Glioblastoma xenografts were developed in mice according to the procedure described in Example 1, using SF-295 cells in lieu of GIST882 cells.

Samples of glioblastoma tumor tissue were harvested from the mice. A Vibratome VT1200 (Leica Microsystems, Wetzlar, Germany) was used to cut thin (300-500 µm) slices from fresh xenograft tissue. The tissue samples were soaked in ice-cold sterile balanced salt solution, orientated, mounted and immobilized using cyanoacrylate glue. To preserve tissue integrity of hollow viscera prior to sectioning, tissue was mounted on polystyrene with the luminal surface facing the Vibratome blade. Slicing speed was optimized according to tissue density and type (0.03-0.08 mm/sec neoplastic tissue; 0.01-0.08 mm/sec normal tissue). Vibration amplitude was set at 2.95-3.0 mm.

Tissue slices were cultured on organotypic inserts for up to 120 h (two slices per insert, Millicell-CM, Millipore, Billerica, Mass., USA). Organotypic inserts are Teflon™ membrane with 0.4 m pores that allow preservation of three dimensional tissue structure in culture. Tissue culture was performed at 37° C. in a 5% CO2 humidified incubator using 1 ml of Ham F-12 media supplemented with 20% inactivated FBS, 100 U/ml penicillin (GIBCO, Invitrigen, Carlsbad, Calif. USA), 100 g/ml streptomycin (GIBCO), 2.5 g/ml amphotericin Band 100 g/ml of Kanamycin (Sigma Aldrich, St. Luis, Mo.). Medium was changed every 2 days.

Tissue viability was assessed using an MTT 1-(4,5-dimethylthiazol-2-yl)-3,5-diphenylformazan assay (Sigma Aldrich). Tissue slices were incubated with 5 mg/ml of MTT at 37° C. for 4 hours, harvested, and precipitated salt extracted by incubation with 0.1M HCl-Isopropyl alcohol at room temperature for 25 min. A viability value was determined by dividing the optical density of the formazan at 570 nm by the dry weight of the explants. Baseline samples (T0) were used as calibrators (IX) to normalize inter-sample variation in absorbance readings and tissue viability was expressed as percentage of viability relative to T0 samples.

Viable tissue cultures were divided into two groups: the first group was treated with 50 ng/mL of NU-1001-41 antibody, and the second group remained untreated. Samples from each were harvested at baseline time (T0) and thereafter at 24 h intervals. A portion of the issue from each group was snap-frozen for qPCR, and another portion was formalin fixed and paraffin embedded (FFPE) for morphological (Haematoxylin and Eosin, H&E) and immunohistochemical (IHC) evaluation.

H&E slides of FFPE material were used to assess the morphological integrity of tissue samples, and to determine the presence of total Akt and p-Akt in the xenograft tissue. Indirect immunoperoxidase analysis was performed on the tissue samples using a commercial phospho-Akt monoclonal antibody (#9271, Cell Signaling, Danvers, Mass., USA) for staining at a dilution of 1:50. Tissue arrays were built as described in Example 2; and five µm sections were cut, dewaxed and incubated in absolute methanol solution with 0.3 ml of hydrogen peroxide for 30 min prior to antigen retrieval (3×5 min., 6 microwave cycles in sodium citrate buffer pH 6.0). Sections then were treated with blocking serum for 10 min after which they were incubated for 2 h up to 12 h with specific primary antibody, and protein detection was performed using peroxidase-conjugated specific secondary antibody (Dako REAL™ HRP secondary antibody system, Dako NA, Carpinteria, Calif.). Antigen-antibody complexes were detected by 3,3'-diaminobenzidine (DAB) and counterstained with haematoxylin. Negative and positive controls were included.

Figure 3A:
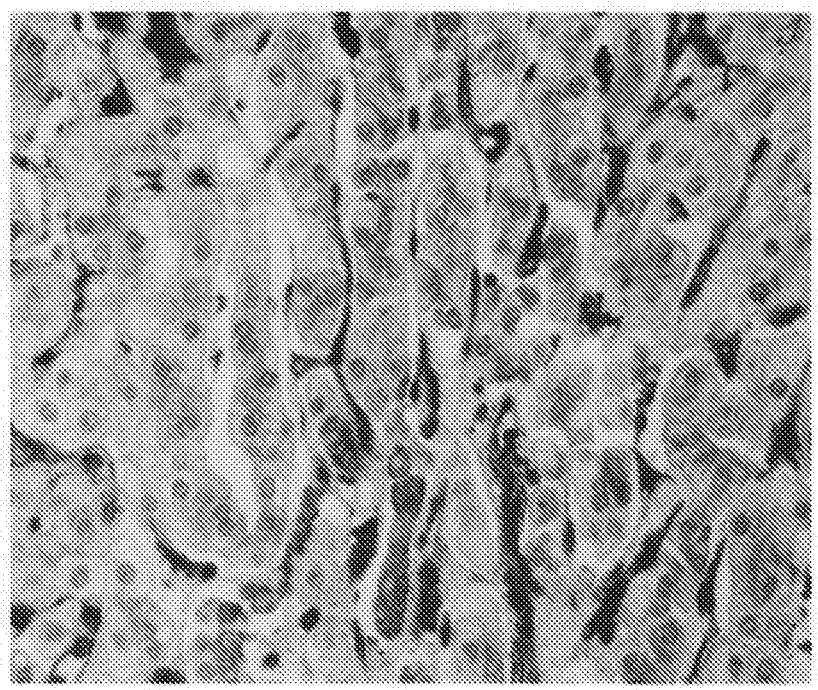
FIGS. 3A and 3B show the staining patterns in glioblastoma xenograft tissue using a commercial p-Akt antibody.
Figure 3B:
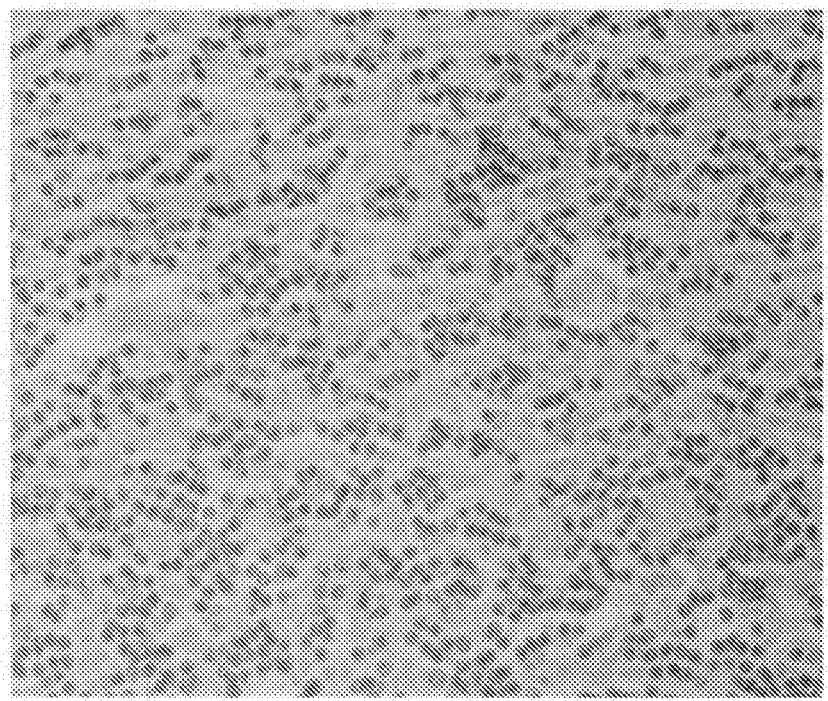

The results are shown in FIGS. 3A and 3B. FIG. 3A shows the staining pattern in the untreated glioblastoma xenograft tissue; a significant amount of staining was observed, indicating the presence of p-Akt in the tissue. FIG. 3B shows the staining patterns for glioblastoma xenograft tissue harvested 24 hours after treatment with MAb NU-1001-41; little or no staining was observed, which indicates that little or no p-Akt is present in the tissue.

P-Akt Inhibition in Glioblastoma Cells

Glioblastoma cells from the SF-295 cell line were grown to confluence in T75 flasks in 10% Dulbecco's Modified Eagle's Medium (DMEM) at 37° C. Once the T75 flask was 100% confluent, cells are trypsinized, transferred with a pipet to a T225 flask and incubated at 37° C. until DO % confluent.

The cells are divided into two groups: the first group was treated with 50 ng/mL of NU-1001-41 antibody, and the second group remained untreated. The cells were harvested 24 hours after treatment according to the following general procedure: the cells in the T225 flasks were trypsinized, pipetted into a 50 ml conical falcon tube and spun down in a centrifuge at 5000 g for 5 minutes to create a pellet. Excess medium was decanted or removed by aspiration, and 20 ml of PBS added to pellet (for cleansing). The 50 ml tube containing the pellet and PBS then was vortexed to break up the pellet and redistribute the cells into the PBS. The 50 ml tube was then spun down at 5000 g for 5 min to create a new and cleaner pellet. The PBS was poured or aspirated off without disturbing the pellet and the 50 ml tube was placed on ice. PBS is added to the cell pellet, and the tube is vortexed to redistribute the cells.

Figure 4A:
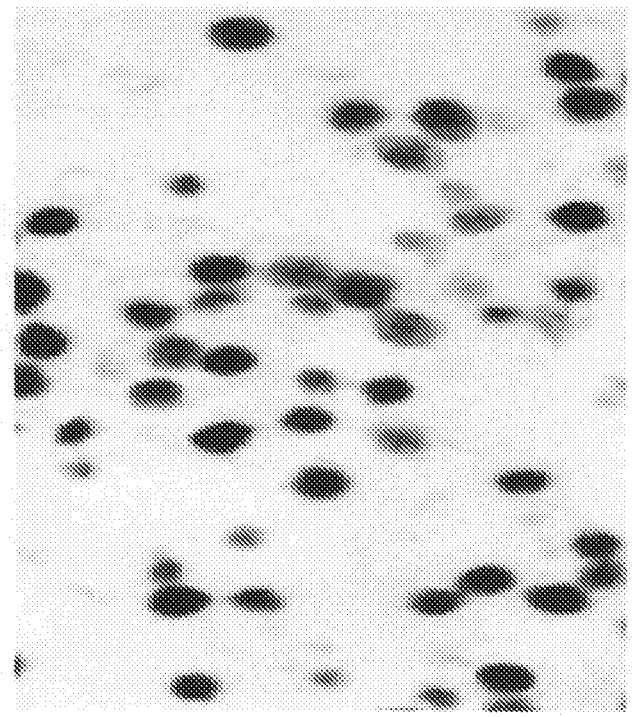
FIG. 4A shows intense staining in untreated tissue.
Figure 4B:
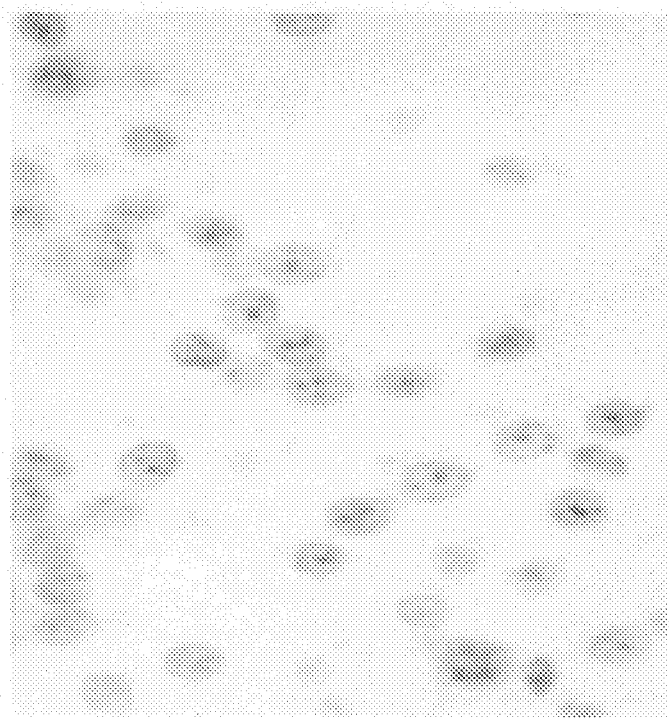

The cells from both treated and untreated groups were pipetted into microtiter wells, and subjected to staining using a commercial p-Akt antibody (Cell Signalling Technology) labeled with a chromogenic stain (KPL Purple, KPL, Inc., Gaithersburg, Md.). The staining patterns are shown in FIGS. 4A and 4B. FIG. 4A shows the staining pattern for untreated cells; the intense color indicates the presence of significant levels of p-Akt. FIG. 4B shows the staining pattern for cells treated with NU-1001-41; the pale color indicated that little or no p-Akt is present.

Figure 5:
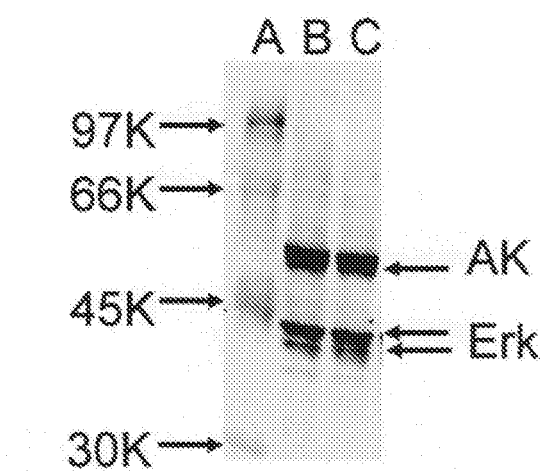
FIG. 5 shows the results of a Western Blot of proteins extracted from glioblastoma cell line SF-295; Lane A contains proteins extracted from SF-295 cells that had been treated for 10 minutes with 50 ng/mL of NU-1001-41 antibody; Lane B contain proteins extracted from untreated SF-295 cells; and Lane C shows protein markers for total AKT and total ERK.

All of the proteins were extracted from the treated and untreated SF-295 cells, and subjected to Western blot analysis to determine the presence and amount of total AKT and ERK present in the cells. The results are shown in FIG. 5: Lane A contains the proteins extracted from the cells treated with NU-1001-41; Lane B contains the proteins extracted from the untreated cells, and Lane C contains protein markers for total AKT and total ERK. As shown in FIG. 5, the untreated cells (Lane B) contain dark bands of protein at the MW markers for AKT and ERK, whereas the cells treated with NU-1001-41 contain no significant proteins at these MWs. These results show that NU-1001-41 inhibits both AKT and ERK.

I claim:

1. A method for detecting the presence or the amount of a phospho-AKT protein in a biological sample comprising,
    (a) contacting the sample with a monoclonal antibody which specifically binds to a phosphorylated epitope within the peptide of SEQ ID NO:5 or SEQ ID NO:6; and
    (b) determining the presence or the amount of phospho-AKT protein bound to the monoclonal antibody,
wherein the monoclonal antibody is obtained by a method comprising the steps of:
    (i) administering to a mammal with at least two peptides, wherein the two peptides consist of the amino acid sequences of SEQ ID NOs: 5 and 6, respectively, and wherein the two peptides are phosphorylated;
    (ii) collecting cells producing the antibody from the mammal; and
    (iii) immortalizing the cells obtained in step (ii) thereby creating a hybridoma expressing the monoclonal antibody.

2. The method of claim 1, wherein the monoclonal antibody is labeled with a detectable label.

3. The method of claim 2, wherein the detectable label is a radiolabel, a fluorescent label, a luminescent label, a bioluminescent label or an enzymatic label.

4. The method of claim 3, wherein the amount of phospho-AKT protein is determined by an immunoassay.

5. The method of claim 4, wherein the immunoassay is selected from the group consisting of radioimmunoassay (RIA), enzyme-linked immunoabsorbent assay (ELISA), immunoprecipitation (IP), immunohistochemistry (IHC), and immunofluorescence (IF).

6. The method of claim 5, wherein the biological sample is obtained from cancerous tissues.

7. The method of claim 1, wherein the two peptides are phosphorylated in at least one serine or threonine residue within the peptides.

* * * * *

SEQUENCE LISTING

```
<160> NUMBER OF SEQ ID NOS: 6

<210> SEQ ID NO 1
<211> LENGTH: 21
<212> TYPE: PRT
<213> ORGANISM: Homo sapiens

<400> SEQUENCE: 1

Phe Tyr Gly Ala Glu Ile Val Ser Ala Leu Asp Tyr Leu His Ser Gly
1               5                   10                  15

Lys Ile Val Tyr Arg
            20

<210> SEQ ID NO 2
<211> LENGTH: 31
<212> TYPE: PRT
<213> ORGANISM: Homo sapiens

<400> SEQUENCE: 2

Asp Lys Lys Leu Val Pro Pro Phe Lys Pro Gln Val Thr Ser Glu Thr
1               5                   10                  15

Asp Thr Arg Tyr Phe Asp Glu Glu Phe Thr Ala Gln Thr Ile Thr
            20                  25                  30

<210> SEQ ID NO 3
<211> LENGTH: 30
<212> TYPE: PRT
<213> ORGANISM: Homo sapiens

<400> SEQUENCE: 3

Gln Trp Thr Thr Val Ile Glu Arg Thr Phe His Val Glu Thr Pro Glu
1               5                   10                  15

Glu Arg Glu Glu Trp Thr Thr Ala Ile Gln Thr Val Ala Asp
            20                  25                  30

<210> SEQ ID NO 4
<211> LENGTH: 33
<212> TYPE: PRT
<213> ORGANISM: Homo sapiens

<400> SEQUENCE: 4

Phe Ser Glu Asp Arg Ala Arg Phe Tyr Gly Ala Glu Ile Val Ser Ala
1               5                   10                  15

Leu Asp Tyr Leu His Ser Glu Lys Asn Val Val Tyr Arg Asp Leu Lys
            20                  25                  30

Leu

<210> SEQ ID NO 5
<211> LENGTH: 18
<212> TYPE: PRT
<213> ORGANISM: Homo sapiens

<400> SEQUENCE: 5
```

```
Phe Val Met Glu Tyr Val Asn Gly Gly Glu Leu Phe Phe His Leu Ser
1               5                  10                 15

Arg Glu

<210> SEQ ID NO 6
<211> LENGTH: 33
<212> TYPE: PRT
<213> ORGANISM: Homo sapiens

<400> SEQUENCE: 6

Glu Asp Ile Lys Phe Pro Arg Thr Leu Ser Ser Asp Ala Lys Ser Leu
1               5                  10                 15

Leu Ser Gly Leu Leu Ile Lys Asp Pro Asn Lys Arg Leu Gly Gly Gly
            20                  25                 30

Pro
```